US005080898A

United States Patent [19]

Murphy

[11] Patent Number: 5,080,898
[45] Date of Patent: Jan. 14, 1992

[54] ENZYMATICALLY ACTIVE TOXIN COUPLED TO A CELL-SPECIFIC LIGAND

[75] Inventor: John R. Murphy, Lexington, Mass.

[73] Assignee: The University Hospital, Boston, Mass.

[21] Appl. No.: 313,599

[22] Filed: Feb. 21, 1989

Related U.S. Application Data

[63] Continuation of Ser. No. 798,163, Nov. 13, 1985, abandoned, which is a continuation-in-part of Ser. No. 795,940, Nov. 6, 1985, Pat. No. 4,675,382, which is a continuation of Ser. No. 667,381, Nov. 1, 1984, abandoned, which is a continuation of Ser. No. 493,775, May 12, 1983, abandoned, which is a continuation-in-part of Ser. No. 337,386, May 12, 1982, abandoned.

[51] Int. Cl.[5] .................... A61K 37/48; A61K 37/54; C12N 15/00; C12N 11/00

[52] U.S. Cl. ................................ 424/94.1; 424/94.6; 424/94.63; 435/174; 435/172.3; 530/807; 530/810; 935/13; 935/14

[58] Field of Search .................... 435/174, 177, 172.3; 935/13, 14; 530/812, 807, 810; 424/94.1, 94.6, 94.63; 536/27

[56] References Cited

U.S. PATENT DOCUMENTS 4,468,382 8/1984 Bacha et al. ........................ 424/177

FOREIGN PATENT DOCUMENTS 8303971 11/1983 PCT Int'l Appl. .
8503508 8/1985 PCT Int'l Appl. .

*Primary Examiner*—David M. Naff
*Attorney, Agent, or Firm*—Fish & Richardson

[57] ABSTRACT

A cell-specific toxin molecule is prepared containing an enzymatically active toxin moiety coupled to a cell-specific binding ligand. The toxin moiety may be a diphtheria toxin, and has a non-naturally occurring cysteine residue encoded by a DNA sequence including a non-naturally occurring cysteine codon. The ligand may be a peptide hormone, proteinaceous growth factor, antibody of steroid hormone, and is derivatized with a sulfhydryl group reactive with the cysteine residue of the toxin moiety to couple the ligand to the toxin moiety via a disulfide bond. Derivatization of the ligand may be by providing the ligand with a non-naturally occurrring cysteine residue encoded by a DNA sequence including a non-naturally occurring cysteine codon. The toxin moiety exhibits cytotoxic activity but fails to exhibit generalized eukaryotic cell binding, and may be used to treat medical disorders.

3 Claims, 5 Drawing Sheets

```
                                                                      290
GLU LYS ALA LYS GLN TYR LEU GLU GLU PHE HIS GLN THR ALA LEU GLU HIS PRO GLU LEU LYS THR VAL THR GLY THR ASN PRO VAL
GAG AAA GCT AAA CAA TAC CTA GAA GAA TTT CAT CAA ACG GCA TTA GAG CAT CCT GAA CTT AAA ACC GTT ACT GGG ACC AAT CCT GTA
              270                                280                                                            330
PHE ALA GLY ALA ASN TYR ALA ALA TRP ALA VAL ALA ASN VAL ALA GLN VAL ILE ASP SER GLU THR ALA ASP LEU GLU LYS THR ALA ALA LEU SER
TTC GCT GGG GCT AAC TAT GCG GCG TGG GCA GTA GCA AAC GTT GCA CAA GTT ATC GAT AGC GAA ACA GCT GAT TTG GAA AAG ACA ACT GCT CTT TCG
              300                                          320
ILE LEU PRO GLY ILE LEU GLY SER VAL MET GLY ILE ALA ASP GLY ALA VAL HIS HIS ASN THR GLU GLN ILE VAL ALA GLN SER ILE ALA LEU SER SER LEU
ATA CTT CCT GGT ATC GGT CTT AGC AGC GTA ATG GGC ATT GCA GAC GGT GCC GTT CAC CAC AAT ACA GAA CAG ATA GTT GCA CAA TCA ATA GCT TTA TCG TCT TTA
                          340                                                    360
                           370                                       390
MET VAL ALA GLN ALA ILE PRO LEU VAL GLY LEU VAL ASP ILE GLY PHE ALA ALA TYR ASN LEU PHE GLN VAL VAL
ATG GTT GCT CAA GCT ATT CCA TTG GTA GGA CTA GTT GAT ATT GGT TTC GCT GCA TAT AAT TTG TTT CAA GTA GTT
                                            380                                       ASN
                                                                                   410 CB44>  PRO(PHE)
HIS ASN SER TYR ASN ARG SER ALA TYR SER PRO GLY HIS ASP TYR  THR GLN LEU HIS ASP ILE THR ALA GLU ASN GLY LYS ILE ARG MET ARG CYS ARG ALA ILE ASP GLY ASP VAL THR PHE
CAT AAT TCG TAT AAT CGT TCC GCC TAT TCT CCG GGG CAT GAC TAT GCT  ACG CAA CCA (TTT) CTT CAT GAC ATT ACT GCT GAA AAT GGT GTA AAA ATA AGG ATG CGT TGC AGA GCT ATA GAC ACT ATT
               400                                       420                                          440                              NruI     460
                                                                                                    450 PRO LEU PRO THR ILE  ILE (SER) VAL LEU LEU PRO THR ILE
                                                                                                        CCA CTT CCA ACT ATT  ATC (GCG) GTC CTA CTA CCG ACT ATT
                                                                                                                                            490
HIS ILE SER VAL ASN GLY LYS LEU THR HIS ILE SER LYS LEU ASP LYS PRO LYS THR LEU ASN GLY VAL HIS ALA PHE HIS SER  SER SER GLU LYS ILE HIS SER ASN GLU
CAT CAT TCC GTA AAT GGT CTT AAG ACT CAT ATT TCC AAG CTG GAC AAG CCT AAA ACA CTG AAT GGT GTG CAT GCG TTT CAC  AGC AGC GAG AAA ATT CAT TCT AAC CAA
                                  470                                 500                          520
                                                                                  510                            540                                    LYS
                                                                                                                                                     550 SER(LEU) PHE PHE GLU ILE LYS SER
PRO GLY LYS LEU ASP PRO VAL TYR VAL ASN GLY PHE GLN LYS VAL ASP HIS THR HIS LYS VAL ASN SER LYS  LEU PHE PHE GLU ILE LYS SER
CCT GGA AAG CTG GAC CCT GTT TAT GTT GGT AAT GGT TAC CAG AAA ACA GAT CAC ACC AAG GTT AAT TCT AAG  CTA TTT TTT GAA ATC AAA AGC
                              480                                                                                   560
                     ASN
CYS ARG PRO LYS SER(ASP) SER ILE GLY VAL LEU GLY
TGT CGC CCT AAA TCT (GAT) TCC ATA GGC GTT CTT GGG
          490                 500
ILE SER SER(ASP) SER ILE GLY VAL LEU GLY TYR GLN LYS VAL ASP HIS THR HIS LYS VAL ASN SER LYS LEU PHE PHE GLU ILE LYS SER  (···)
ATT TCG TCG (GAT) TCC ATA GGC GTT CTT GGG TAC CAG AAA ACA GAT CAC ACC AAG GTT AAT TCT AAG CTA TTT TTT GAA ATC AAA AGC  (TCA)  1800

1800
AAGGTAG TGGGGTCGTG TGCCGGTAAG CGGAACGGTT CCGGAATGGC GCTATAGTAT GCACAGGTAG AGCAGAATTC GAATCTGACT ACGGATCAGA AGGTTGGGGG TTCGAATCCC TCC
      1700←                          ←                                                                                          ←       1800

GGGCGCA CAAGTGAAAC CCCAGCTCAT AGCATGTTTG AGCTGGGGT TCTCATGGCG TGTGGGTTGT CTGACTGTTG GCTGTTGTTG CGGTGGTTGG TGCTCGTACC GAACCGAACG
                                                                                                                           1900
```

ENZYMATICALLY ACTIVE TOXIN COUPLED TO A CELL-SPECIFIC LIGAND

This application is a continuation of U.S. Pat. Ser. No. 06/798,163, Nov. 13, 1985, abandoned, which is a continuation-in-part of U.S. Pat. Ser. No. 06/795,940, Nov. 6, 1985, U.S. Pat. No. 4,675,382, which is a continuation of Ser. No. 06/667,381, Nov. 1, 1984, abandoned, which is a continuation of U.S. Pat. Ser. No. 06/493,775, May 12, 1983, abandoned, which is a continuation-in-part of U.S. Pat. Ser. No. 06/377,386, May 12, 1982, abandoned.

BACKGROUND OF THE INVENTION

This invention was made in part with government funding and the government has certain rights in the invention.

This invention relates to the use of recombinant DNA techniques to make analogs of toxin molecules, and to the use of such molecules to treat medical disorders.

The literature contains a number of examples of hybrid molecules containing a specific binding ligand-portion and a toxin portion (e.g., ricin or diphtheria toxin); the ligand targets the toxin to an unwanted class of cells, sparing healthy cells, to which the ligand fails to bind.

For example, Bacha et al. U.S. Pat. No. 4,468,382 (hereby incorporated by reference) describes hybrid molecules made by derivatizing a neuropeptide hormone (e.g., thyrotropin releasing hormone) and an enzymically active fragment of diphtheria toxin using sulfur-containing groups and then reacting the derivatized molecules to join them via a disulfide bond. One disadvantage of this approach is that the site of derivatization on both molecules cannot be precisely controlled, so that the final product is heterogeneous, containing some molecules in which derivatization and coupling has impaired the toxicity or binding capacity of the hybrid molecule.

An approach which deals with this problem of heterogenicity is described in Murphy PCT International Publication No. WO/83/03971 (hereby incorporated by reference). The Murphy application describes hybrid proteins encoded by genes encoding both the toxin and the specific binding portion of the hybrid protein. This approach, of course, can be used only for DNA-encoded peptide ligands.

SUMMARY OF THE INVENTION

The present invention provides toxin molecules which can be linked to any specific-binding ligand, whether or not it is a peptide, at a position which is predeterminedly the same for every toxin molecule.

The invention generally features, in one aspect, a DNA sequence encoding a fragment of a toxin molecule which is large enough to exhibit cytotoxic activity and small enough to fail to exhibit generalized eucaryotic cell binding; the DNA sequence includes a non-naturally occurring cysteine codon, preferably located such that the fragment encoded by the DNA sequence, when linked to a cell-specific ligand via the cysteine residue encoded by the cysteine codon, exhibits cytotoxic enzymic activity.

In preferred embodiments, the toxin is diphtheria toxin, ricin, or abrin; the cysteine codon is introduced at the C-terminal-encoding end of the toxin-encoding DNA sequence or within 100 base pairs thereof; the ligand is a peptide hormone, a proteinaceous growth factor (preferably Interleukin I, Interleukin II, Interleukin III, or B-cell growth factor), an antibody, or a steroid hormone (e.g., estradiol).

In another aspect, the invention features a specific binding peptide ligand, and DNA sequences coding therefor, which can bind to any reactive sulfur group-containing toxin molecule in a predetermined and consistent manner. The DNA sequence of this aspect of the invention encodes a fragment of a ligand (preferably one of those listed above) which is large enough to exhibit specific cell binding; the gene includes a non-naturally occurring cysteine codon, preferably located such that the fragment encoded by the DNA sequence, when linked to a toxin via the cysteine residue encoded by the cysteine codon, exhibits specific cell binding.

The invention also features the hybrid molecules made using the Cys-modified toxins and ligands of the invention, as well as the methods for making such hybrid molecules.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIGS. 7A and 7B show the nucleotide sequence of the tox$^{228}$ allele and flanking regions, with amino acid residues shown above nucleotides; the tox$^{228}$ allele is the same as the wild-type tox allele except for several mutations, notably the presence on the tox$^{228}$ allele of an NruI site (FIGS. 7A and 7B were adapted from FIG. 1 of Kaczorek et al. (1983) Science 221, 855).

TOX GENE

The tox gene, and the diphtheria toxin molecule it encodes, will now briefly be described.

Figure 2:
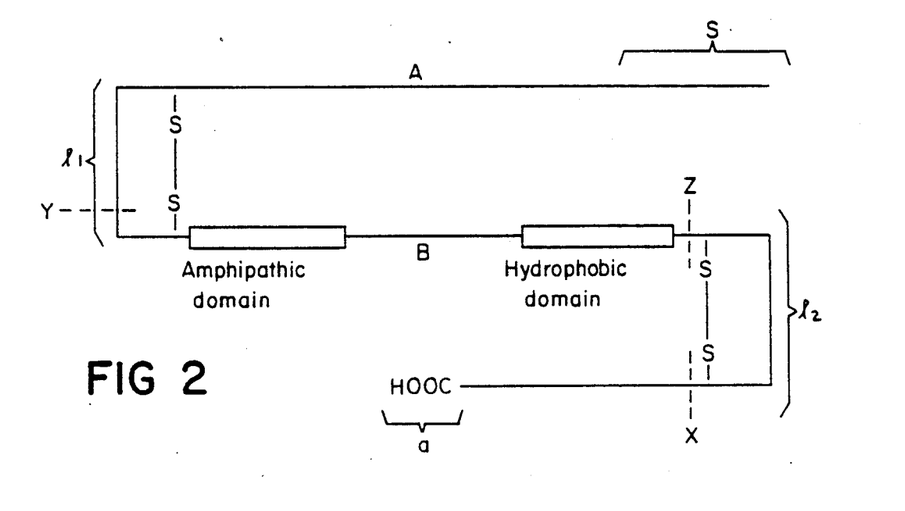
FIG. 2 is a diagrammatic representation of the diphtheria toxin molecule.
Figure 3:
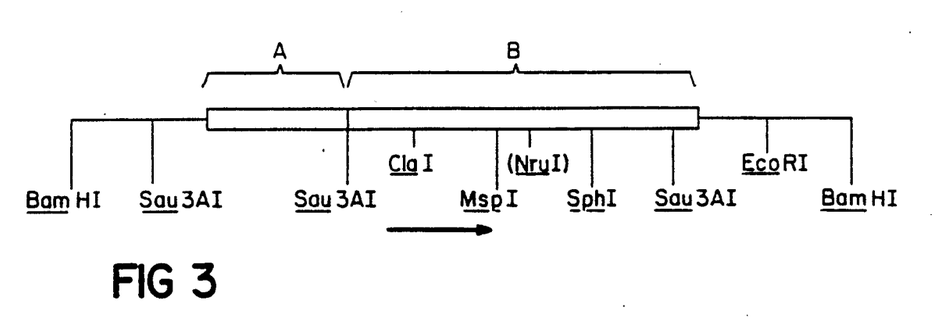
FIG. 3 is a restriction map showing the location and orientation of the diphtheria tox gene on the 3.9 BamHI-I restriction fragment of corynephage beta$^{tox}$.
Figure 4:
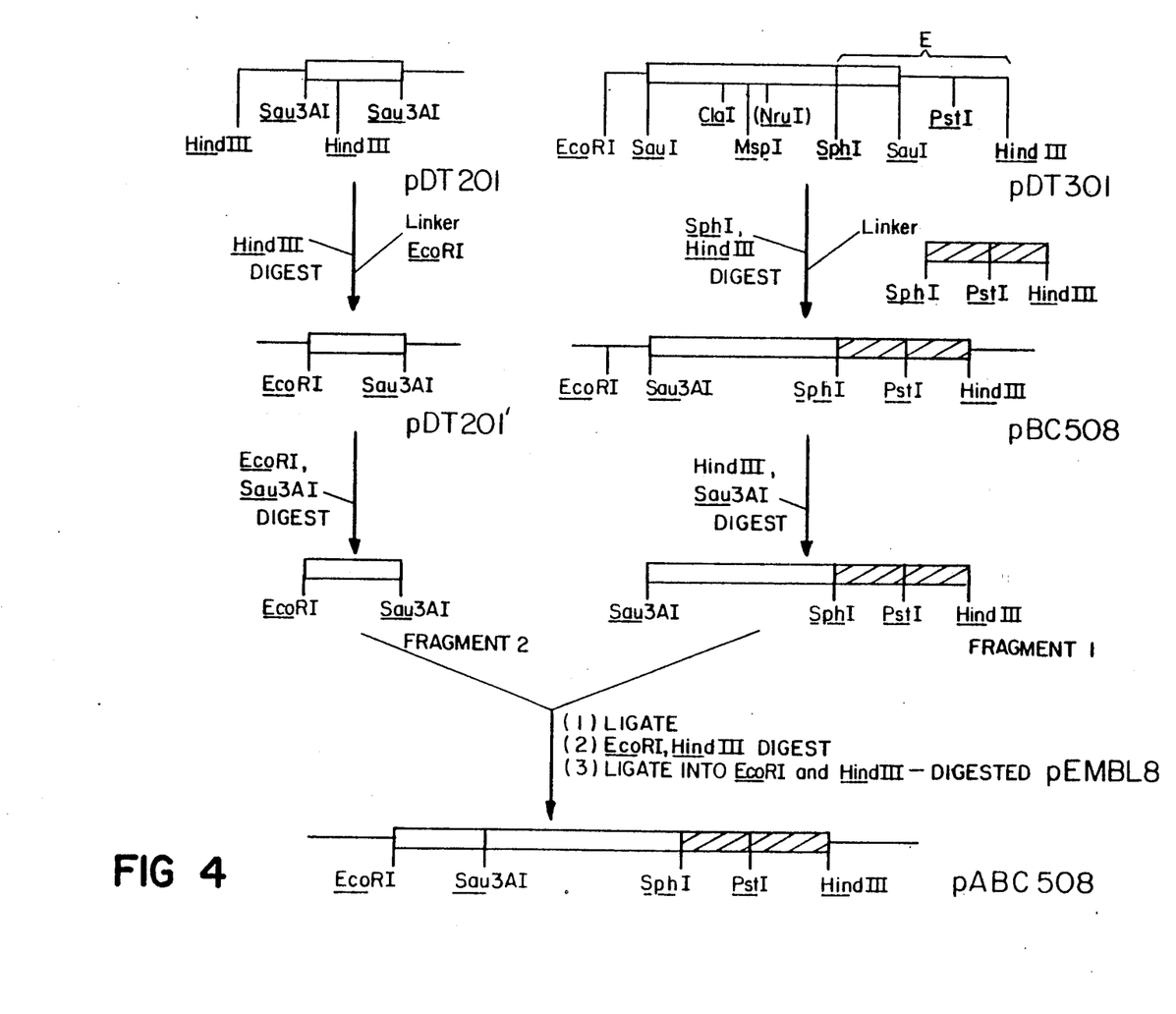
FIGS. 4–5 are diagrammatic representations of the steps involved in the construction of pABC1508.
Figure 5:
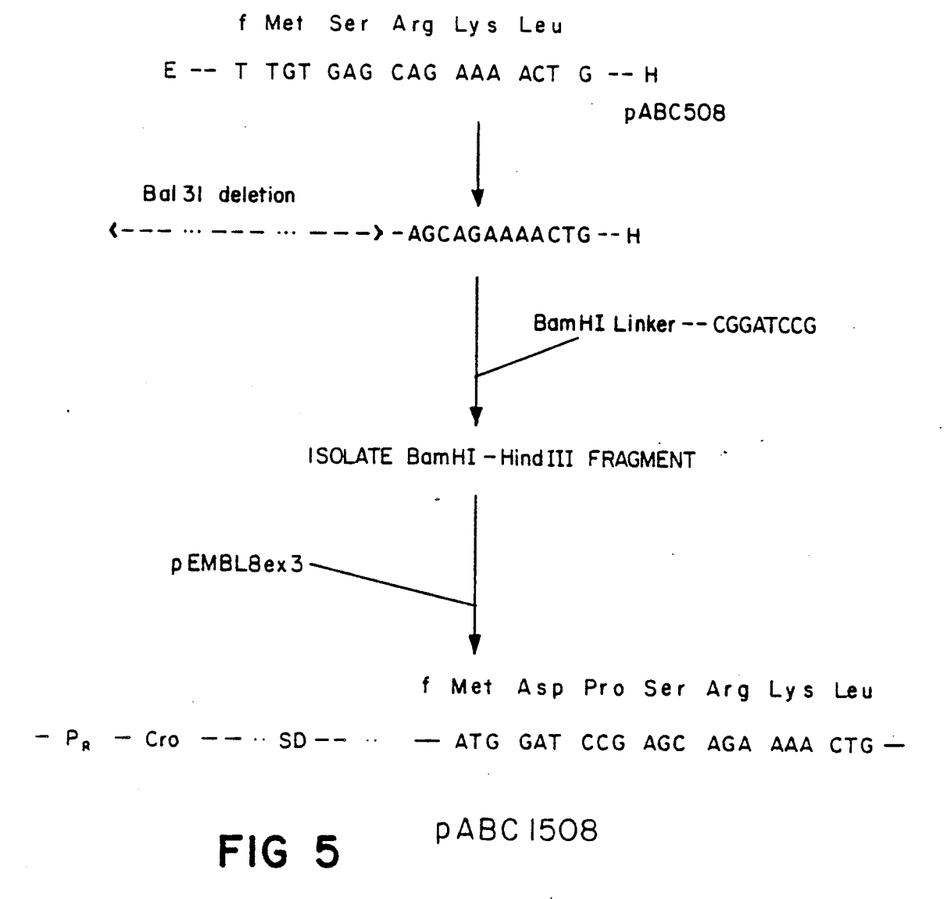
Figure 6:
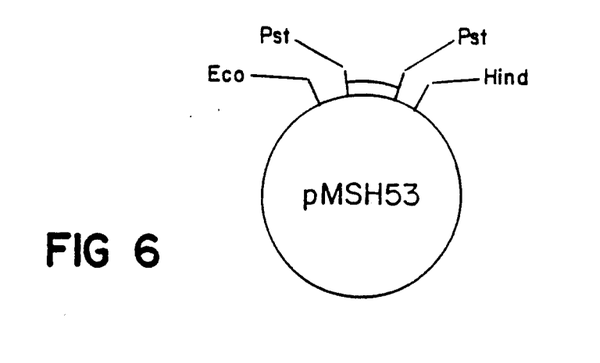
FIG. 6 is a diagrammatic representation of a plasmid, pMSH53 containing α-MSH-encoding DNA.

FIGS. 2 and 3, illustrate, respectively, the diphtheria toxin molecule and the diphtheria tox gene, located on the 3.9 kb BamHI restriction fragment of corynephage beta$^{tox}$. FIGS. 7A and 7B give the sequence of the tox$^{228}$ allele.

Referring to FIG. 2, the diphtheria toxin molecule consists of several functional "domains" which can be characterized, starting at the amino terminal end of the molecule, as a hydrophobic signal sequence; enzymically active Fragment A, the fourteen amino acid exposed protease sensitive disulfide loop (DSL) $1_1$, containing a cleavage domain; Fragment B, which includes the lipid associating regions, e.g., a hydrophilic amphipathic domain and a hydrophobic domain; DSL $1_2$; and carboxy terminal end a. DSL$1_1$ contains three arginine residues; the Sau3Al site between Fragment A and Fragment B (see FIG. 3) is at a position on the diphtheria toxin gene corresponding to the arginine residue farthest downstream of the three.

The process by which diphtheria toxin intoxicates sensitive eukaryotic cells involves at least the following steps: (i) diphtheria toxin binds to specific receptors on the surface of a sensitive cell; (ii) while bound to its receptor, the toxin molecule is internalized in an endocytic vesicle; (iii) either prior to internalization, or within the endocytic vesicle, the toxin molecule may be cleaved (or processed) at a site in the region of 47,000 daltons from the N-terminal end; (iv) as the pH of the endocytic vesicle decreases to below 5.5, the processed form of toxin, while still bound to its receptor, spontaneously inserts into the endosomal membrane; (v) once embedded in the membrane, the lipid associating regions form a pore; (vi) a proteolytic cleavage in $1_1$, between Fragment A and B, occurs; (vii) thereafter, Fragment A, or a polypeptide containing Fragment A, is released into the cytosol; (viii) the catalytic activity of Fragment A, i.e., the nicotinamide adenine dinucleotide-dependent adenosine diphosphate ribosylation of Elongation Factor 2, causes the death of the intoxicated cell. It is apparent that a single molecule of Fragment A introduced into the cytosol is sufficient to kill a cell.

Modified Tox Gene

Figure 1:
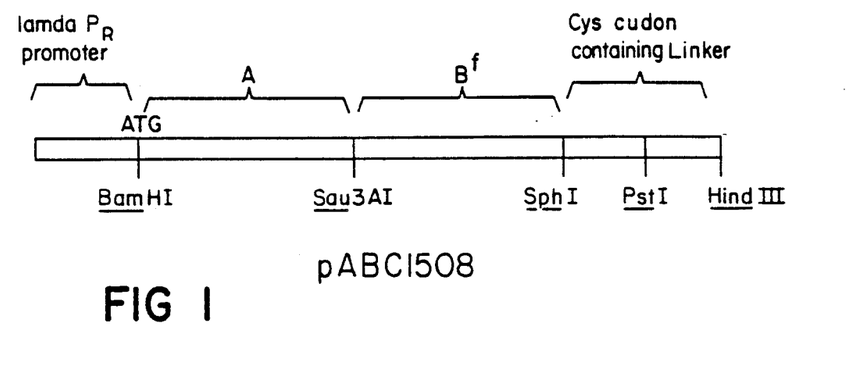
FIG. 1 is a partial restriction map of a DNA fragment of the invention, in plasmid pABC1508.

Referring to FIG. 1, there is shown the region of plasmid pABC1508 which encodes a peptide of the invention.

The DNA region shown in FIG. 1 includes the lambda $P_R$ promoter (substituted for the promoter naturally associated with the tox gene); an ATG initiation site; a DNA sequence encoding enzymically active Fragment A of diphtheria toxin; a portion of the DNA region encoding Fragment B of diphtheria toxin; and a linker containing a Cys codon.

Referring to FIGS. 1–3, the portion of the diphtheria tox gene used to make a DNA sequence of the invention includes the region encoding enzymically active Fragment A (and preferably the hydrophobic leader sequence preceding Fragment A), and a portion of the Fragment B-encoding region at least as long as that ending at the MspI site. As shown in FIG. 3, the Fragment A-encoding region (including the leader sequence) begins just downstream from a convenient Sau3AI site. The MspI site is the approximate location of the end of the region of the tox gene which encodes cross reacting material 45 (CRM 45), described in Bacha et al., id. This portion of the diphtheria toxin molecule contains the lipid associating regions of Fragment B, but does not contain $1_2$, and is represented in FIG. 2 as the portion of Fragment B between y and z. The Fragment B-encoding region employed can end anywhere beyond MspI, up to the SphI site. If the SphI site is used, $1_2$ is included, and the portion of Fragment B is that between y and x in FIG. 3. As previously mentioned, any region ending between MspI and SphI can be used; one example is the region ending at the position of NruI, which, like the region ending at MspI, encodes a Fragment which does not contain $1_2$. Any region shorter than one ending at MspI should not be used because such a fragment will not include enough of the transverse lipid associating region and thus not bring about pore formation, which is necessary for toxicity. Portions of Fragment B encoded by regions ending downstream of SphI should not be used to avoid including the diphtheria toxin receptor binding domain. (NruI is not found on the wild-type tox allele, but only on the mutant tox[228] allele, described in Kaczorek et al. (1983) Science 221, 855.) The sequence of tox[228] allele is shown by FIGS. 7A and 7B.

In the illustrated DNA construct (FIG. 1) the Cys codon is located at the C-terminal end of the tox-encoding DNA sequence. This location ensures that the linker containing the Cys codon will not interfere with the enzymic activity of Fragment A. Other locations in the molecule which are downstream from the Fragment A encoding region can also be used, i.e., the Cys codon-containing linker can be inserted anywhere in the Fragment B-encoding region.

Other toxins which are DNA- encoded amino acid chains can be used, in addition to diphtheria toxin; examples are ricin and the plant toxin abrin.

Ligands

The specific-binding ligands used in the invention can consist of an entire ligand, or a portion of a ligand which includes the entire binding domain of the ligand, or an effective portion of the binding domain. It is most desirable to include all or most of the binding domain of the ligand molecule. In the case of alpha-MSH, a small peptide of thirteen amino acids, or beta-MSH, which contains seventeen amino acids, the portion of the molecule consisting of nine amino acids at the carboxy terminal end of the molecule, which contains the receptor-specific binding domain, can be used, or, more preferably, the entire molecule can be used. It is most preferred that at least a portion of the ligand not involved in cell binding be included, so that derivatization can be carried out in this nonbinding portion, minimizing the chance that derivatization will interfere with binding. For example, derivatization of alpha-MSH is preferably carried out at or near the N-terminal end of the molecule, because the C-terminal end contains the specific binding domain.

The regions within cell-specific ligands in which the binding domain is located are now known for a number of such ligands. Furthermore, recent advances in solid phase polypeptide synthesis can enable those skilled in this technology to determine the binding domain of practically any peptide ligand, by synthesizing various fragments of the ligand, and testing them for the ability to bind the class of cells to be killed.

The specific class of cells which are bound and killed by the hybrids of the invention is determined by the specific ligand which imparts the binding domain of the hybrid molecule. Any cell-specific ligand can be used which has a binding domain which is specific for a particular class of cells which are to be killed. Polypeptide hormones are useful such ligands. Hybrid proteins made using alpha- or beta-MSH, for example, can selectively bind to melanocytes, rendering the hybrids useful in the treatment of primary melanoma and metastic melanoma loci. Other specific-binding ligands which can be used include the proteinaceous growth factors interleukin I, interleukin II, interleukin III, and B-cell growth factor. Interleukin II is of particular importance because of its role in allergic reactions and autoimmune diseases such as Systemic Lupus Erythromatosis (SLE), involving activated T cells. Hybrids made using B-cell growth factor can be used as immunosuppressant reagents which kill proliferating B-cells, which bear B-cell growth factor receptors, and which are involved in hypersensitivity reactions and organ rejection.

The other major class of specific binding proteins are antibodies. The antibodies most useful are those against tumors; such antibodies (generally monoclonal) are already well-known targeting agents used in conjunction with covalently bound cytotoxins. In the present invention, the anti-tumor antibodies (preferably not the whole antibody, but just the Fab portion) are those which recognize a surface determinant on the tumor cells and are internalized in those cells via receptor-mediated endocytosis; antibodies which are capped and shed will not be as effective.

Other useful polypeptide ligands having cell-specific binding domains are somotostatin, follicle stimulating hormone (specific for ovarian cells); luteinizing hormone (specific for ovarian cells); thyroid stimulating hormone (specific for thyroid cells); vasopressin (specific for uterine cells, as well as bladder and intestinal cells); prolactin (specific for breast cells); and growth hormone (specific for certain bones cells).

Peptide hormones must be derivatized with a sulfhydryl group reactive with the Cys of the toxin molecule. This can be carried out by inserting a Cys codon-containing linker into an appropriate location in a DNA sequence encoding the hormone, in a manner analogous to that described below for the tox gene. Alternatively, a sulfhydryl group, either by itself or as part of a Cys residue, can be introduced using solid phase peptide synthesis techniques. For example, the introduction of sulfhydryl groups into peptides is described in Hiskey (1981) Peptides 3, 137. Derivatization can also be carried out according to the method described for the derivatization of the peptide hormone thyrotropin releasing hormone in Bacha et al. U S. Pat. No. 4,468,382, id. Similarly, proteins can be derivatized at the DNA or protein chemistry level. The introduction of sulfhydryl groups into proteins is described in Maasen et al. (1983) Eur. J. Biochem. 134, 2, 32.

The major class of non-peptide specific binding ligands useful in the invention are the steroid hormones. One example is estrogen and estrogen derivatives such as estradiol; these are currently used in the treatment of prostate carcinoma and post-menopausal mammary carcinoma. Hybrids containing these hormones, or analogs thereof, can be used in the same or smaller dosages, to treat the same diseases. The derivatization of steroid hormones can be carried out using standard techniques, such as those described in Ikagawa et al. (1981) J. Org. Chem. 46, 18, 3747. For example, the steroid hormone 17-beta-estradiol can be derivatized, substituting an SH group for a hydroxyl group, to yield

Gene Construction

Generally, plasmids are manipulated according to standard techniques. Plasmid DNA is digested with restriction endonucleases as recommended by the manufacturer (e.g., New England Biolabs, Beverly, Mass.). Restriction fragments are electrophoresed in 1% horizontal agarose gels for 30-60 minutes at 80-100 V in TBE (89 mM boric acid, 89 mM Trizma base [Sigma Chemical Co., St. Louis, Mo.], 2.5 mM EDTA, pH 7.0) in the presence of 200 ng/ml ethidium bromide. Small DNA fragments are electrophoresed in 8% vertical polyacrylamide gels at 100 V for 2-5 hours, and stained with ethidium bromide. Gels are photographed on an ultraviolet transilluminator on Polaroid type 667 film using a red filter.

Plasmid pABC508 was constructed by fusing two pieces of DNA, one encoding Fragment A, and the other encoding part of Fragment B, to which a Cys codon-containing linker had been attached.

Referring to FIG. 4, this fusion was constructed from two plasmids, pDT201, which contains the fragment A-encoding region, and pDT301, which contains most of the fragment B-encoding region of the diphtheria toxin gene. The construction of each of these pieces of DNA is described below.

Plasmid pDT301 was constructed by cutting out of the tox allele a Sau3AI-1 sequence encoding all but the C-terminal 17 amino acids of Fragment B. This sequence, which carries the restriction endonuclease sites ClaI, MspI, and SphI. was inserted into the BamHI site of plasmid pUC8 (described in Viera et al. (1982) Gene 19, 259) to yield pDT301. Plasmid pDT201 contains the Fragment A-encoding Sau3AI-2 sequence (FIG. 3) (see Leong et al. (1983) Science 220, 515). (pDT301 and pDT201, in *E. coli*, have been deposited in the American Type Culture Collection, Rockville, MD and given ATCC Accession Nos., respectively, 39360 and 39359. Applicant's licensee, Seragen, Inc., acknowledges its responsibility to replace these cultures should they die before the end of the term of a patent issued hereon, and its responsibility to notify the ATCC of the issuance of such a patent, at which time the deposits will be made available to the public for a period of at least 30 years after the date of deposit. Until that time the deposits will be made available to the Commissioner of Patents under the terms of 37 CFR §1.14 and 35 USC §112.)

Still referring to FIG. 4, plasmid pDT301 was modified by the addition of a Cys codon-containing linker as follows. A synthetic linker was constructed on a controlled pore glass solid phase support in a 380A DNA Synthesizer (Applied Biosystems, Inc., Foster City, Calif.) by hybridization of 21-mer and 29-mer oligonucleotides through a 21 bp homologous core, leaving a 4bp ½ SphI and ½ HindIII single-stranded sequence on each end. This linker has the sequence

```
             Ala  Ala  Ala  Cys  Stp
          5'-CGGCTGCAGCATGTTAGTAGA-3'
      3'-GTACGCCGACGTCGTACAATCATCTTCGA-5'
  ½ SphI          PstI                  ½ HindIII
```

The linker encodes three alanine residues, and contains a Cys codon (TGT) and a Stop codon (TAG). (This design not only allows for the expression of a Cys-containing peptide according to the present invention, but also could allow for the insertion at the PstI site of a gene encoding a specific binding ligand.)

As shown in FIG. 4, pDT301 was digested with SphI and HindIII to remove the DNA region designed "E" in FIG. 4, and the Cys codon-containing linker was then ligated into the Plasmid at the SphI, HindIII sites to give plasmid pBC508. pBC508 was then cut with HindIII and Sau3AI to give Fragment 1.

Still referring to FIG. 4, plasmid pDT201 was digested with HindIII and the single-stranded ends filled in with DNA polymerase I (Klenow fragment). The resulting blunt ends were ligated to the double-stranded EcoRI linkers

```
CCTTAAGG
GGAATTCC
```

(New England Biolabs, Beverly, Mass.) to give pDT201', which was then cut with EcoRI and Sau3A to give Fragment 2.

Fragments 1 and 2 were mixed in equimolar concentrations ligated together, according to standard procedures, and the mixture was then digested with EcoRI and HindIII. The digested mixture was then ligated into the EcoRI and HindIII digested pEMBL8 (Dente et al. (1983) Nucleic Acid Res. 11, 1645), which contains unique EcoRI and HindIII sites, to give pABC508. Plasmid pABC508 can be transformed into a suitable host, e.g., *E. coli*, as described below, to produce Cys-modified toxin molecules.

Alternatively, the naturally occurring tox promoter can be replaced with a different promoter, as follows.

The lambda $P_R$ promoter is contained in the expression vector pEMBL8ex3 (Dente et al., id). Referring to FIG. 5, the DNA sequence around the initiation site of the tox gene is shown, as are the corresponding amino acids. pABC508 was cut with EcoRI and then treated with Ba131 for a period of 10–15 minutes at 37° C. with one unit of enzyme per microgram of DNA. The resulting mixture of DNA fragments was ligated to the BamHI linkers

CCTAGGCC,
GGATCCGG transformed into *E. coli* HB101 (Bethesda Laboratories, Gaithersburg, MD), and the DNA sequence of the region encoding the 5' end of tox, and the sequence of 30 of the resulting clones determined One clone, containing the DNA sequence shown in FIG. 5, was purified and the BamHI-HindIII fragment isolated and inserted into pEMBL8ex3 which had been cut with BamHI and HindIII. The resulting plasmid, pABC1508, contains the lambda $P_R$ promoter and an ATG translational start codon. An extra asparagine and proline residue are inserted during this process. In FIG. 5, Cro represents the Cro gene of lambda, and SD represents the Shine-Dalgarno sequence. The lambda $P_R$ promoter can be regulated by the lambda cI gene. In this example the mutant $cI_{857}$ temperature-sensitive repressor gene is used such that the $P_R$ promoter is inactive at 30° C. and active at 37° C.

pABC1508 was transformed, using conventional techniques (e.g., as described in Maniatis et al. (1984) Molecular Cloning: A Laboratory Manual, Cold Spring Harbor, N.Y.), into *E. coli* HB101 (others, e.g., *E. coli* JM101 or 5Y327, can also be used) and the expression of the diphtheria tox gene products analyzed. The introduction of the positively charged asparagine residue in the tox signal sequence does not affect the export of the tox polypeptides into the periplasmic compartment of the recombinant host.

*E. coli* cells transformed with vectors containing Cys-modified toxin-excoding DNA are grown under standard culture conditions, e.g., in Luria Broth containing, per liter, 10 g tryptone, 10 g NaCl, and 5 g yeast extract, and supplemented with 100 μg/ml ampicillin. The diphtheria toxin-related molecules, which are exported to the periplasmic space, are purified from periplasmic extracts. Periplasmic extracts are prepared from cells grown in 9.5 liter volumes at 37° C. to an $A_{590}$ of approximately 1.0. If the natural tox promoter has been replaced with temperature sensitive cI857 regulatory sequences under the control of the temperature-sensitive $cI_{857}$ gene, as described herein, cells are grown at 30° C., and expression is induced by increasing the incubation temperature to 42° C. for 15 min. The culture is then grown at 40° C. for an additional hour. In either instance, the culture is concentrated to approximately 1 liter by filtration through 0.45μ membranes (Pellicon system, Millipore Corp., Bedford, Mass.) and chilled to 4° C. Bacteria are harvested by centrifugation, resuspended in ice cold 20% sucrose, 30 mM Tris-HCl, 1 mM EDTA, pH 7.5, and then digested with lysozyme (750 μg/ml final concentration) for 30 minutes. Spheroplasts are removed by centrifugation, 2 mg p-amidinophenylmethylsulfonylfluoride (p-APMSF, Calbiochem, San Diego, Calif.) is added, and the periplasmic extract is sterilized by filtration through 0.2μ membranes.

The Cys-modified toxin-related molecules are then purified by chromatography on Phenyl-Sepharose (Pharmacio Fine Chemicals, Piscataway, N.J.) and DEAE-cellulose essentially as described by Rappuoli et al. (1985) Biotechnology, p. 165. Periplasmic extracts are dialysed against 10 mM sodium phosphate (pH 7.2) buffer, and ammonium sulfate added to 13% (w/v). The crude extracts are then applied to a Phenyl-Sepharose column equilibrated with 10 mM phosphate buffer containing 13% ammonium sulfate. The modified toxin is eluted and dialysed against 10 mM phosphate buffer, and then applied to DEAE-cellulose column. After washing with phosphate buffer, the DEAE-cellulose column is developed with a linear NaCl gradient in phosphate buffer.

The modified toxin is then applied to an anti-diphtheria toxin immunoaffinity column, containing antibody made as described in Zucker et al. (1984) Molecular Immunol. 21, 785. Following extensive washing, the modified toxin is eluted with 4 M guanidine hydrochloride, and immediately dialysed against phosphate buffer. The purified modified toxin is then concentrated to approximately 100 μg/ml by placing the dialysis bag in dry Sephadex G-200. All purification procedures are carried out at 4° C., and the modified toxin is stored in small aliquots at −76° C. until used.

Specific Binding Ligand: Alpha-MSH

Referring to FIG. 6, there is shown plasmid pMSH53, which contains a DNA insert encoding alpha-MSH. pMSH53 was made by inserting into pUC8 an alpha-MSH-encoding sequence having a ½ PstI site at each end:

5' GCAAGTTATAGCATGGAACATTTTAGATGGGGAAAACCTGTATAGCTGCA 3'
3' ACGTCGTTCAATATCGTACCTTGTAAAATCTACCCCTTTTGGACATATCG 5'
½ PstI ½ PstI

Plasmid pMSH53 can be used to create, using conventional methods, an expression vector for the production of alpha-MSH in cultured bacterial cells e.g., *E. coli*. Further, prior to such expression, a Cys-containing linker can be fused to or near the N-terminal end of the alpha-MSH-encoding sequence, in a manner analogous to the method described above for the tox gene, to produce a modified alpha-MSH containing an N-terminal Cys capable of reacting with the added Cys of the diphtheria toxin fragment Alternatively, the Cys-containing MSH molecule can be chemically linked to any toxin molecule on which a reactive sulfhydryl group is present or has been added post-translationally, i.e., at the protein chemistry, not the DNA, level.

Rather than making alpha-MSH using recombinant DNA techniques as described above, alpha-MSH can be purified from biological sources, or obtained commercially (e.g., from Sigma Chemical Co., St. Louis, Mo.).

Chemical Linkage

After an available Cys has been added to the ligand by genetic engineering techniques, or if the ligand contains an available reactive Cys or other sulfur-containing group, the toxin and ligand are coupled by reducing both compounds and mixing toxin and ligand, in a ratio of about 1:5 to 1:20, and the disulfide reaction is allowed to proceed at room temperature to completion (generally, 20 to 30 minutes). The mixture is then dialyzed extensively against phosphate buffered saline to remove unreacted ligand molecules. The final purification step involves the separation, on the basis of size, of the desired toxin-hormone conjugates from toxin-toxin and hormone-hormone dimers; this is done by carrying out, in Phosphate-buffered saline, Sephadex G100 chromotography.

Use

The hybrid toxin-ligand molecules are administered to a mammal, e.g., a human, suffering from a medical disorder, e.g., cancer, characterized by the presence of a class of unwanted cells to which the ligand can selectively bind. The amount of hybrid molecule administered will vary with the type of disease, extensiveness of the disease, and size and species of the mammal suffering from the disease. Generally, amounts will be in the range of those used for other cytotoxic agents used in the treatment of cancer, although in certain instances lower amounts will be needed because of the specificity of the molecules.

The hybrid molecules can be administered using any conventional method; e.g., via injection, or via a timed-release implant. The hybrid proteins can be combined with any non-toxic, pharmaceutically-acceptable carrier substance.

In the case of MSH hybrids, topical creams can be used to kill primary melanoma cells, and injections or implants can be used to kill metastatic cells.

Estradiol hybrids, exhibiting binding specificity for certain breast cancers characterized by cells bearing estradiol receptors, can be used to treat primary and metastatic cells.

Other embodiments are within the following claims.

I claim:

1. A cell-specific toxin molecule comprising an enzymatically active toxin moiety coupled to a cell-specific protein or peptide ligand moiety, wherein said toxin moiety exhibits cytotoxic activity but fails to exhibit generalized eukaryotic cell binding, said toxin moiety having a non-naturally occurring cysteine residue encoded by a DNA sequence including a non-naturally occurring cysteine condon, wherein said toxin moiety and said protein or said peptide ligand are coupled via a disulfide bond between the cysteine residue encoded by said non-naturally occurring cysteine condon and a non-naturally occurring cysteine residue of said cell-specific protein or peptide ligand encoded by a DNA sequence including a non-naturally occurring cysteine codon.

2. The toxin molecule of claim 1 wherein said cell specific protein is Interleukin I, Interleukin II, Interleukin III, or B-cell growth factor.

3. The toxin molecule of claim 1 wherein said toxin is diphtheria toxin.

* * * * *